United States Patent
Alur et al.

(10) Patent No.: US 10,039,709 B2
(45) Date of Patent: Aug. 7, 2018

(54) BIOADHESIVE COMPOSITIONS FOR EPITHELIAL DRUG DELIVERY

(75) Inventors: Hemant H. Alur, Basking Ridge, NJ (US); James A. H. Harwick, Tallassee, AL (US); Mondal Pravakar, Kansas City, MO (US); Thomas P. Johnston, Overland Park, KS (US)

(73) Assignee: TRILOGIC PHARMA LLC, Tallassee, AL (US)

( * ) Notice: Subject to any disclaimer, the term of this patent is extended or adjusted under 35 U.S.C. 154(b) by 0 days.

(21) Appl. No.: 13/701,934

(22) PCT Filed: Jun. 2, 2011

(86) PCT No.: PCT/US2011/038906
§ 371 (c)(1),
(2), (4) Date: Feb. 6, 2013

(87) PCT Pub. No.: WO2011/153334
PCT Pub. Date: Dec. 8, 2011

(65) Prior Publication Data
US 2013/0131166 A1    May 23, 2013

Related U.S. Application Data

(60) Provisional application No. 61/351,399, filed on Jun. 4, 2010.

(51) Int. Cl.
  *A01N 37/12*   (2006.01)
  *A01N 37/44*   (2006.01)
  *A61K 31/24*   (2006.01)
  *A61K 9/00*    (2006.01)
  *A61K 31/245*  (2006.01)

(52) U.S. Cl.
  CPC ............ *A61K 9/0002* (2013.01); *A61K 9/006* (2013.01); *A61K 31/245* (2013.01)

(58) Field of Classification Search
  None
  See application file for complete search history.

(56) References Cited

U.S. PATENT DOCUMENTS

| | | | | |
|---|---|---|---|---|
| 5,624,906 | A * | 4/1997 | Vermeer | A61K 8/60 514/23 |
| 6,068,851 | A * | 5/2000 | Bergeron | A61K 9/0014 424/422 |
| 6,432,415 | B1 | 8/2002 | Osborne et al. | |
| 2002/0176827 | A1 * | 11/2002 | Rajaiah | A61C 19/063 424/49 |
| 2006/0115502 | A1 * | 6/2006 | Geloen et al. | 424/401 |
| 2007/0042044 | A1 | 2/2007 | Fischer et al. | |
| 2008/0025926 | A1 * | 1/2008 | Kavouklis | A61K 8/22 424/53 |
| 2008/0253976 | A1 * | 10/2008 | Scott et al. | 424/49 |

FOREIGN PATENT DOCUMENTS

WO    WO2009/001092    12/2008

OTHER PUBLICATIONS

Gorman, Scientific America, Gonorrhea Could Join Growing List of Untreatable Diseases, Feb. 8, 2012.*
Ahn et al. "Slow eroding biodegradable multiblock poloxamer copolymers." Polym Int. 54:842-847, 2005.
Miller et al. "Degradaation rates of oral resorbable implants (polylactates and polyglycolates): rate modification with changes in PLA/PGA copolymer rations." J Biomed Mater REs. 11:711-9, 1977.
Jeong et al. "Thermoreversible gelation of PEG-PLGA-PEG triblock copolymer aqueous solutions." Macromolecules 32:7064-7069, 1999.

* cited by examiner

*Primary Examiner* — Daniel M Podgorski
(74) *Attorney, Agent, or Firm* — Clark G Sullivan

(57) ABSTRACT

Disclosed are compositions and methods for treating a disease, such as infection, pain, or inflammation, by using the compositions. Particularly, disclosed is a method of treating oral pain, wherein, the above-described compositions are applied to the oral mucosa; the compositions undergo in-situ gelation, optimal adhesion to the oral mucosa, controlled erosion and controlled release of the active ingredient, i.e., benzocaine, which provides a superior degree of pain relief or analgesia for an extended period of time.

18 Claims, 2 Drawing Sheets

BIOADHESIVE COMPOSITIONS FOR EPITHELIAL DRUG DELIVERY

CROSS-REFERENCE TO RELATED APPLICATIONS

This application claims benefit of U. S. Provisional Application No. 61/351,399, filed Jun, 4, 2010. Application No. 61/351,399 is hereby incorporated herein by reference in its entirety.

FIELD OF THE INVENTION

The present invention is in the field of bioadhesive compositions useful for the delivery of drugs to epithelial tissue. The compositions dissolve and elute a pharmaceutically active ingredient over an extended period of time, which provides an improved treatment to diseases, particularly to oral pain, where an improved degree of analgesia or pain relief is achieved.

BACKGROUND OF THE INVENTION

Controlled release systems for drug delivery are often designed to administer drugs in specific areas of the body. In this regard, it is critical that the drug not be entrained beyond the desired site of action and eliminated before it has had a chance to exert a topical effect or to pass into the bloodstream. If a drug delivery system can be made to adhere sufficiently to a cavity or a tissue of a body, its contents will be delivered to the targeted cavity or tissue as a function of proximity and duration of the contact.

Oral pain due to cavities, canker sores, dentures, braces, teething and cold sores is not only discomforting, but also annoying. This necessitates a need for an instant pain relief product, but drug delivery to the oral mucosa is challenging. Success directly depends on the residence and contact time between the product and the absorbing mucosa, and these have been some of the drawbacks of existing marketed products. Therefore, there is a need to develop a composition for drug delivery wherein the composition is bioadhesive, bioerodible, biodissolvable and biocompatible. Such a composition has the ability to undergo in-situ gelation, controlled erosion, and optimal mucosal adhesion, and thus address the challenges of oral mucosal delivery and overcome the drawbacks of existing commercial products.

SUMMARY OF THE INVENTION

Disclosed are compositions and methods for treating a disease, such as infection, pain, or inflammation, by using the compositions. Particularly disclosed are compositions and methods of treating oral pain, wherein the compositions are applied to the oral mucosa; the compositions undergo in-situ gelation, optimal adhesion to the oral mucosa, controlled erosion, and controlled release of the active ingredient, i.e., benzocaine, which provides a superior degree of pain relief or analgesia for an extended period of time.

An exemplary composition is bioadhesive, bioerodible, biodissolvable and biocompatible, wherein the composition comprises:
 a) from about 30 to about 70 weight parts of water;
 b) from about 10 to about 30 weight parts of polyethylene glycol (PEG) and/or from about 1 to about 10 weights parts of ethyl alcohol;
 c) from about 10 to about 25 weight parts of a copolymer having the following block structure:

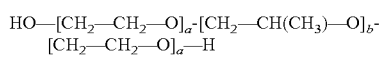

wherein the ratio of a:b is from about 1:1 to about 3:1, and the molecular weight of said copolymer is from about 9000 to about 16000; and
 d) from about 0.1 to about 3.0 weight parts of xanthan gum.

The composition further comprises a therapeutically effective amount of one or more active ingredients, wherein the relative weight parts of said active ingredient is from about 0.5 to about 40. The composition can be applied to any epithelial tissue of a subject as a viscous liquid and solidifies upon exposure to the body temperature of the subject. The composition dissolves over a prescribed period of time and elutes a pharmaceutically active ingredient. The composition can also form a seal with the skin or mucosa surrounding the cavity or tissue to prevent the entry of bacterial pathogens.

Also disclosed are methods of treating a disease to a subject in need, comprising delivering a pharmaceutical composition to a body cavity or a tissue of the subject wherein said pharmaceutical composition is the above-described composition. The method comprises:
 a) providing said composition;
 b) providing epithelial tissue of said subject; and
 c) applying said composition to said tissue, whereupon said composition adheres to and covers said tissue, and gradually elutes drug to said tissue.

DETAILED DESCRIPTION OF THE INVENTION

Figure 1:
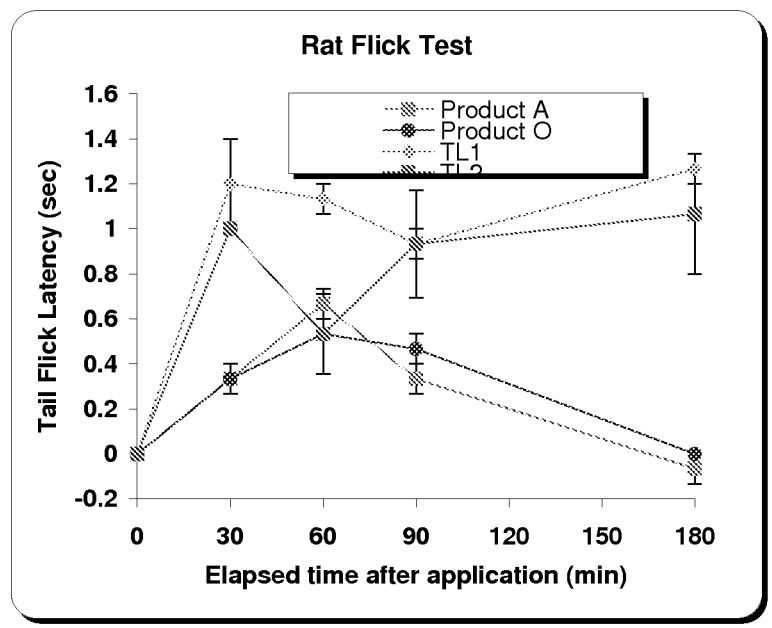
FIG. 1 presents a comparison of the efficacy of two representative compositions of the present disclosure (TL1 and TL2) against two prevalent commercial compositions (Product A and Product O) using the rat-tail flick test to assess nociception.

Before the present compositions, articles, devices, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular embodiments only, and is not intended to be limiting.

Definitions And Use of Terms

As used in this specification and in the claims which follow, the singular forms "a," "an" and "the" include plural referents unless the context clearly dictates otherwise. Thus, for example, reference to "an ingredient" includes mixtures of ingredients, reference to "an active pharmaceutical agent" includes more than one active pharmaceutical agent, and the like.

"Pharmaceutically acceptable" means that which is useful in preparing a pharmaceutical composition that is generally safe, non-toxic and neither biologically nor otherwise undesirable, and includes that which is acceptable for human pharmaceutical use.

"Therapeutically effective amount" means that amount which, when administered to an animal for treating or preventing a disease, is sufficient to effect such treatment or prevention for the disease.

"Subject" means an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

"Comprise" and variations of the word, such as "comprising" and "comprises," means "including, but not limited to," and is not intended to exclude, for example, other additives, components, integers or steps.

By "treating" or "treatment" is meant the medical management of a patient with the intent to cure, ameliorate, stabilize, or prevent a disease, pathological condition, or disorder. These terms include active treatment, that is, treatment directed specifically toward the improvement of a disease, pathological condition, or disorder, and also includes causal treatment, that is, treatment directed toward removal of the cause of the associated disease, pathological condition, or disorder. These terms can mean that the symptoms of the underlying disease are reduced, and/or that one or more of the underlying cellular, physiological, or biochemical causes or mechanisms causing the symptoms are reduced.

When ranges are given by specifying the lower end of a range separately from the upper end of the range, it will be understood that the range can be defined by selectively combining any one of the lower end variables with any one of the upper end variables that is mathematically possible.

When used herein the term "about" or "ca." will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent in humans to the recited strength of a claimed product.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions

Disclosed are compositions comprising:
a) from about 30 to about 70 weight parts of water;
b) from about 10 to about 30 weight parts of polyethylene glycol (PEG) and/or from about 1 to about 10 weights parts of ethyl alcohol;
c) from about 10 to about 25 weight parts of a copolymer having the following block structure:

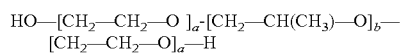

wherein the ratio of a:b is from about 1:1 to about 3:1, and the molecular weight of said copolymer is from about 9000 to about 16000; and
d) from about 0.1 to about 3.0 weight parts of xanthan gum.

In some forms, the composition can be a composition wherein weight parts of the water is from about 30 to about 65. In other forms, the weight parts of the water in the composition is from about 35 to about 60, or from about 40 to about 60, or from about 40 to about 45.

In some forms, the composition can be a composition, wherein, weight parts of the polyethylene glycol is from about 10 to about 30, from about 15 to about 25, or about 20. In some forms, the composition can be a composition wherein, the polyethylene glycol is selected from the group consisting of PEG 200, PEG 300, PEG 400, PEG 600, PEG 1000, PEG 4000, PEG 6000, and PEG 8000. In other forms, the composition can be a composition wherein the polyethylene glycol is PEG 200. Exemplary PEGs are provided in the following Table 1.

TABLE 1

| Composition | Av. Molecular weight | Appearance | Melting point (° C.) |
|---|---|---|---|
| PEG 200 | 190-210 | Oily liquid | |
| PEG 300 | 285-315 | Oily liquid | |
| PEG 400 | 380-420 | Oily liquid | |
| PEG 600 | 570-630 | Oily liquid | 17-22 |
| PEG 1000 | 950-1050 | Solid | 35-40 |
| PEG 4000 | 3800-4400 | Solid | 53-58 |
| PEG 6000 | 5600-6400 | Solid | 55-60 |
| PEG 8000 | 7500-8500 | Solid | 58-65 |

In some forms, the composition can be a composition, wherein, weight parts of ethyl alcohol is from about 1 to about 10, from about 2 to about 8, or from about 4 to about 6. In some forms, the composition can further comprise a therapeutically effective amount of one or more active ingredients. The active ingredient can be selected from the group consisting of analgesics, local anesthetics, antimicrobials, antibiotics, antibacterials, anti-inflammatories, and anti-infectives. Therapeutically effective amounts of these active ingredients can be released in a controlled manner in a range from about 1 to 60 minutes, from about 1 to 24 hours, or from about 1 to 20 days following application. In some forms, the composition can be a composition, wherein, weight parts of the active ingredient is from about 0.5 to about 40, from about 5 to about 40, from about 10 to about 40, from about 15 to about 35, from about 20 to about 35, or about 20.

Analgesic drugs that can be incorporated into the composition include acetaminophen, ibuprofen, methylsalicylate, menthol, camphor, methylnicotinate, triethanolamine salicylate, glycol salicylate, or salicylamine. Local anesthetics that can be incorporated into the composition include lidocaine hydrochloride, oxybuprocaine hydrochloride, procaine, benzocaine, xylocaine, etidocaine, cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, and mepivacaine.

Suitable antimicrobials include iodine, povidone iodine, benzalkonium chloride and chlorhexidine gluconate. Suitable antibacterial drugs include the beta-lactam antibiotics, tetracyclines, chloramphenicol, clindamycin, neomycin, gramicidin, bacitracin, polymixin, sulfonamides, aminoglycoside antibiotics, tobramycin, nitrofurazone, nalidixic acid and analogs, and combinations thereof. Suitable anti-inflammatories include cortisone, hydrocortisone, betamethasone, dexamethasone, fluocortolone, prednisolone, triamcinalone, indomethacine, sulindac and its salts and corresponding sulfide. Suitable anti-infectives include bifonazole, siccanin, bisdequalinium acetate, clotrimazole, salicylie acid, sulfamethoxazole sodium, erythromycin and gentamicin sulfate.

In some forms, the composition can be a composition wherein the active ingredient is a local anesthetic. In other forms, the composition can be a composition wherein the local anesthetic is benzocaine.

In some forms, the composition can be a composition wherein weight parts of the copolymer is from about 5 to about 30, from about 10 to about 20, or from about 15 to about 20. In some forms, the copolymer can be Poloxamers, which are non-ionic, triblock copolymers of the following general structure:

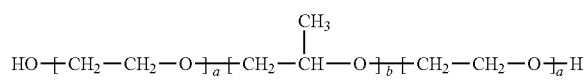

The structure consists of a hydrophobic central core of propylene oxide (represented by "b" in the above figure), flanked by hydrophilic ethylene oxide (represented by "a" in the above figure) on both sides. Poloxamers are soluble in water and other polar and non-polar solvents and are regarded as chemically inert. Commercially, poloxamers are available from BASF as flakes (denoted by "F"), paste (denoted by "P"), liquid (denoted by "L") and micronized (denoted by "micro"). Their chemical composition and specifications are provided below in Tables 2 and 3.

Poloxamers show temperature dependent thermoreversible properties. Poloxamer 407 (F127) is the most well studied poloxamer for this behavior. Generally, this behavior has been studied in 20-30% w/w aqueous solutions, which are liquid at low temperature (2-5° C.) and turn into gel at room temperature (22-25° C.). This gelation temperature is dependent on the molecular weight and the percentage of the hydrophobic portion, hence, the gelling temperature decreases as both the molecular weight and the hydrophobic fraction increases. In general, the gelation temperature increases in the order of F127<F108<F 87<F68<F44. The gelation temperature can also be modulated by varying the percentage of F127, or mixing it with one or more other poloxamers. The three pharmaceutically relevant (due to availability and approved for use in pharmaceutical products) poloxamers are F127, F108, and F68. Because of all of their interesting and useful physical properties, poloxamers can be used in a pharmaceutical composition to function as a completely biocompatible and bioerodible drug delivery implant, and that meet demanding requirements such as controlled drug release, controlled erosion, body clearance, viscosity at room temperature, and adhesion to biological surfaces.

In some forms, the composition can be a composition wherein the poloxamer is selected from the group consisting of poloxamer 124, poloxamer 188, poloxamer 237, poloxamer 338 and poloxamer 407. In other forms, the composition can be a composition wherein the poloxamer is poloxamer 407.

In some forms, the composition can be a composition, wherein, weight parts of the xanthan gum is from about 1 to about 3, or from about 1.5 to about 2.0. Xanthan gum refers to a high molecular weight polysaccharide used as a food additive and rheology modifier. It may be produced by a process involving fermentation of glucose or sucrose by the *Xanthomonas campestris* bacterium. The backbone of the polysaccharide chain consists of two β-D-glucose units linked through the 1 and 4 positions. The side chain consists of two mannose and one glucuronic acid, so the chain consists of repeating modules of five sugar units. The side chain is linked to every other glucose of the backbone at the 3 position. About half of the terminal mannose units have a pyruvic acid group linked as a ketal to its 4 and 6 positions. The other mannose unit has an acetyl group at the 6 positions. Two of these chains may be aligned to form a

TABLE 2

| Pluronic ® | Poloxamer | a | b | Content of Oxyethylene (Percent) | Molecular Weight |
| --- | --- | --- | --- | --- | --- |
| L44NF | 124 | 12 | 20 | 44.8-48.6 | 2090-2360 |
| F68NF | 188 | 80 | 27 | 79.9-83.7 | 7680-9510 |
| F87NF | 237 | 64 | 37 | 70.5-74.3 | 6840-8830 |
| F108NF | 338 | 141 | 44 | 81.4-84.9 | 12700-17400 |
| F127NF | 407 | 101 | 56 | 71.5-74.9 | 9840-14600 |

TABLE 3

| | Poloxamer | | | | |
| --- | --- | --- | --- | --- | --- |
| | 124 | 188 | 237 | 338 | 407 |
| Physical Form | Liquid | Solid | Solid | Solid | Solid |
| pH (2.5% in water) | 5.0-7.5 | 5.0-7.5 | 5.0-7.5 | 5.0-7.5 | 5.0-7.5 |
| Cloud point, 10% | 71-75° C. | >100° C. | >100° C. | >100° C. | >100° C. |
| APHA color | 50 max. | 100 max. | 100 max. | 100 max. | 120 max. |
| % H$_2$O | 0.4 max. | Cast solid 0.4 max. | Cast solid 0.4 max. | Cast solid 0.4 max. | Cast solid 0.4 max. |
| | | Prill 0.75 max. | Prill 0.75 max. | Prill 0.75 max. | Prill 0.75 max. |
| BHT, ppm | — | 50-125 | 50-125 | 50-125 | 50-125 |
| Unsaturation mEq/g | 0.020 ± 0.008 | 0.026 ± 0.008 | 0.034 ± 0.008 | 0.031 ± 0.008 | 0.048 ± 0.017 |
| Ethylene Oxide, ppm | 1 max. | 1 max. | 1 max. | 1 max. | 1 max. |
| Propylene Oxide, ppm | 5 max. | 5 max. | 5 max. | 5 max. | 5 max. |
| 1,4 dioxane, ppm | 0.002% max. | 0.002% max. | 0.002% max. | 0.002% max. | 0.002% max. | double helix, giving a rather rigid rod configuration that accounts for its high efficiency as a viscosifier of water. The molecular weight of xanthan varies from about one million to 50 million depending upon how it is prepared. In some forms, the molecular weight of the xanthan ranges from approximately 1 to 25 million, as measured by a Brookfield Viscometer. In some other forms, the molecular weight is 1, 2, 3, 4, or 5±0.5, or 6, 7, 8, 9, 10, 11, 12, 13, 14, 15, 16, 17, 18, 19, 19, 20, 21, 22, 23, 24, or 25±2 million.

In some forms, the composition can be a composition comprising:
a) from about 40 to about 45 weight parts of water;
b) from about 15 to about 25 weight parts of polyethylene glycol, and/or from about 3 to about 6 weights parts of ethyl alcohol;
c) from about 15 to about 20 weight parts of poloxamer 407;
d) from about 1.5 to about 2.5 weight parts of xanthan gum; and
e) about 20 weight parts of benzocaine.

In other forms, the composition can be a composition comprising:
a) about 41.5 weight parts of water;
b) about 20 weight parts of polyethylene glycol, and/or or about 4 weights parts of ethyl alcohol;
c) about 16.5 weight parts of poloxamer 407;
d) about 2.0 weight parts of xanthan gum; and
e) about 20 weigh parts of benzocaine.

In other forms, the composition can be a composition comprising:
a) about 43.5 weight parts of water;
b) about 20 weight parts of polyethylene glycol, and/or or about 4 weights parts of ethyl alcohol;
c) about 15 weight parts of poloxamer 407;
d) about 1.5 weight parts of xanthan gum; and
e) about 20 weigh parts of benzocaine.

In other forms, the composition can be a composition which further comprises one or more conventional pharmaceutical excipients selected from the group consisting of stabilizers, antioxidants, buffers and pH regulating agents. In some forms, the composition can be a composition further comprising a taste masking agent.

In some forms, the composition can be a composition, wherein, the composition is applied to a bodily cavity or a tissue of a subject. The bodily cavity can be dental sulci, a surgical incision, or a wound. The tissue refers to a collection of cells. Tissue is a cellular organizational level intermediate between cells and a complete organism. Hence, a tissue is an ensemble of cells, not necessarily identical, but from the same origin, that together carry out a specific function. In other forms, the composition can be a composition, wherein, the composition is applied to the oral mucosa of a subject.

In some forms, the composition can be a composition, wherein, the composition is an in-situ gel composition after implanted into a bodily cavity or applied on a tissue of said subject. The composition exists at a viscosity that can be easily inserted into a body cavity or applied on a tissue, and, subsequently, remains in place for the viscous liquid to solidify. The implants, which result from the insertion, dissolve in adjacent aqueous-based extracellular fluids at a predictable rate over an extended period of time, elute the active ingredient at a controlled rate, provide a barrier against entry of infectious pathogens, and are completely cleared and excreted from the body via normal pathways of elimination (mainly in the urine).

In some forms, the composition is bioadhesive, bioerodible, biodissolvable and biocompatible. In other forms, the composition can be a composition, wherein, the composition imparts extended adhesion to the body cavity or the tissue in the subject. In other forms, the composition can be a composition, wherein, the composition is eroded at a substantially constant rate. In some forms, the composition can be a composition, wherein, the active ingredient is released from the composition at a controlled rate over a prolonged period of time. In other forms, the composition can be a composition, wherein, the active ingredient is released from the composition at a zero-order rate (which means that a constant amount, as opposed to a constant percent or fraction, of the active ingredient is released per unit of time) In other forms, the composition can be a composition, wherein, the release of said active ingredient from the composition is released in a sustained manner. In other forms, the composition can be a composition, wherein, the composition is eliminated by the body of the subject. In some forms, the subject is a mammal In summary, the composition can convert to a solid or semi-solid gel in situ when injected into a cavity or applied to a tissue of a subject; the resulting gel is bioadhesive, so it can remain in contact with the cavity or the tissue, and/or seal the skin or mucosa together from within the cavity, to form a barrier against further bacterial invasion; the gel is bioerodible, so it dissolves in adjacent extracellular fluids over time and release the active ingredient in a controlled manner; and the gel is biodissolvable, so once it has dissolved, it can be processed via normal elimination pathways (mainly in the urine) and excreted from the human body.

In other forms, the composition is free or mass flowing, so that it may be administered through a syringe with a needle or other suitable device. A suitable syringe volume may range from 1 to 25 millimeters, and be injected using a needle ranging from 16 to 25 gauge. The incision or wound can be closed by any suitable mechanical structure, such as sutures, adhesive strips, or biocompatible glue.

Methods

The above-described compositions are useful for treating diseases to a subject in need. Accordingly, in some forms, disclosed are methods of treating a disease to a subject in need, comprising delivering a pharmaceutical composition to a body cavity or a tissue of said subject, wherein, said pharmaceutical composition is any one of the above-described compositions.

In some forms, the method of treating a disease can be a method which comprises:
a) providing said composition;
b) providing a body cavity or a tissue of said subject; and
c) forming a barrier against pathogen entry into said cavity or said tissue by applying said composition to said cavity or said tissue, whereupon said composition gels in the form of an implant and adheres to said cavity or said tissue around the entire periphery of said cavity or said tissue.

In other forms, the method of treating a disease can be a method, wherein, the composition turns to be a gel at a temperature between room temperature and the body temperature of said subject; has a capacity to adhere to said cavity or said tissue when implanted into said cavity or applied on said tissue; and has a capacity to bioerode and elute said active ingredient.

In some forms, the method of treating a disease can be a method, wherein, the disease is selected from the group consisting of infection, pain, and inflammation. In other forms, the method of treating a disease can be a method, wherein, the disease is oral pain. In some forms, the method of treating a disease can be a method, wherein, the oral pain is due to cavities, canker sores, dentures, braces, teething or cold sores. In other forms, the method of treating a disease can be a method, wherein, the method provides an improved adhesive capacity of the above-described compositions on said cavity or tissue. In other forms, the method of treating a disease can be a method, wherein, the subject is a mammal.

In summary, disclosed are methods of treating diseases to a subject in need, wherein, the above-described compositions are delivered to a body cavity or a tissue of said subject; the compositions then transforms to a gel and adheres to the body cavity or the tissue; the gel undergoes erosion and releases the active ingredients, which provides improved degree of instant treatment of the diseases; and the treatment can be sustained for an extended period of time. Particularly, disclosed is a method of treating oral pain, wherein, the above-described compositions are applied to oral mucosa; the compositions undergo in-situ gelation, optimal adhesion to the oral mucosa, controlled erosion, and controlled release of the active ingredient, i.e., benzocaine, which provides a superior degree of pain relief or analgesia for an extended period of time.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Compositions Tested In the Examples

Polyethylene glycol (PEG) was used as a solvent to incorporate benzocaine. Bezocaine and PEG were mixed and warmed to ~90-95° C. to dissolve benzocaine. Poloxamer and xanthan gum were dissolved in water, which was then added to bezocaine and PEG mixture with constant stirring. PEG could be replaced with ethyl alcohol in any of the examples described. Representative compositions according to the present disclosure (i.e., TL1 and TL2) are shown in Table 4.

TABLE 4

Composition Details

| Ingredients | TL1 [% (w/w)] | TL2 [% (w/w)] | TL3 [% (w/w)] |
| --- | --- | --- | --- |
| Benzocaine, USP | 20.0 | 20.0 | 20.0 |
| PEG 200, USP | 20.0 | 20.0 | — |
| Poloxamer 407, USP | 16.5 | 15.0 | 16.5 |
| Xanthan gum, USP | 2.0 | 1.5 | 2.0 |
| Water, qs | 41.5 | 43.5 | 61.5 |

Composition details of the prevalent commercial compositions (i.e., product A and product O) used in the examples are shown below:

Product A: Benzocaine 20%, benzyl alcohol, carbomer 934P, D&C yellow no. 10, FD&C blue no. 1, FD&C red no. 40, glycerin, methylparaben, natural and artificial flavor, polyethylene glycol, propylene glycol, saccharin (U.S. Pat. No. 6,344,480); and Product O: Benzocaine 20%, cellulose gum, gelatin, menthol, methyl salicylate, pectin, plasticized hydrocarbon gel, polyethylene glycol, and sodium saccharin.

Comparative Study of Efficacy

The efficacy of the representative compositions according to the present disclosure (TL1 and TL2) was evaluated against two prevalent commercial compositions (Product A and Product O) using the rat-tail flick test (FIG. 1). FIG. 1 shows that TL1 and TL2 not only produce higher degree of analgesia, but also provide a much higher degree of analgesia for an extended period of time relative to Product A and Product O. In this regard, the area under the tail flick latency curve, which denotes rate and extent, was 3-4 times higher for TL1 and TL2 than for that of Product A and Product O (Table 5). In rat-tail flick test, the time taken for the rat to flick it's tail due to heat is noted when the tail is immersed in hot water. Briefly, a water bath was equilibrated at 52° C. The formulation was applied to the base of the tail of a rat. Then at different time points the tail was immersed in the water bath equilibrated at 52° C. The time taken by the rat to flick its tail was noted. Baseline was collected before starting the experiment without applying the formulations. Tail flick time for each formulation was determined in a minimum of three rats. The tail flick latency times were then determined by subtracting the baseline value at each time point, averaged and reported as the mean±the standard deviation.

Comparative Study of Release Profile

Figure 2:
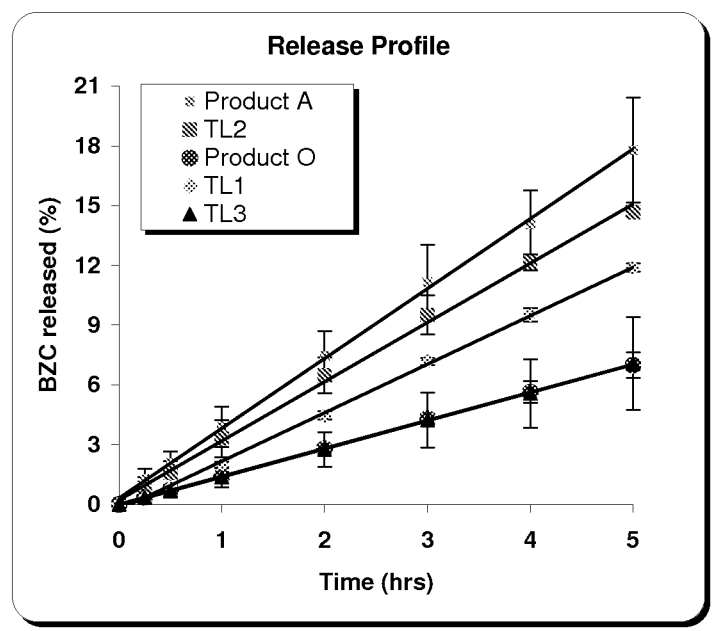
FIG. 2 illustrates the release profile of an active ingredient from two representative compositions of the present disclosure (TL1 and TL2) and two prevalent commercial compositions (Product A and Product O).

FIG. 2 shows that the release of the active ingredient from the representative compositions according to the present disclosure (TL1 and TL2) is almost similar to that of Product A and Product O. The release rate of TL1 and TL2 varied from about 2.5 to about 3%/hr under controlled conditions (Table 5). Nearly 1 g of the formulation was placed inside a dialysis cassette (Slide-A-Lyzer 3.5K) with a molecular weight cut off of 3500 daltons. The cassette was immersed in 180 ml of deionized water. At different time points, entire content of the beaker was replaced with fresh 180 ml of deionized water, which was analyzed for benzocaine using HPLC. Release of benzocaine from each formulation was determined a minimum of three times. The % benzocaine released was then averaged and reported as the mean±the standard deviation.

Comparative Study of Adhesive Strength

Figure 3:
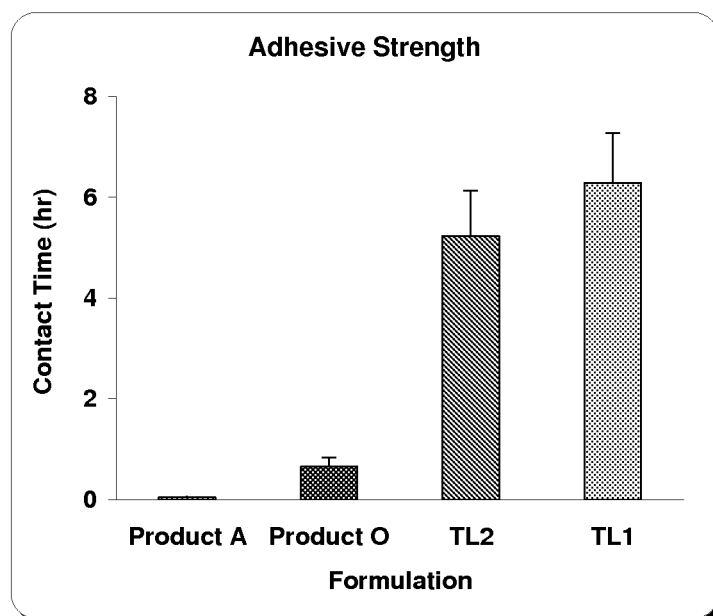
FIG. 3 presents a comparison of adhesive strength to a body cavity or a tissue (measured in terms of contact time) of two representative compositions of the present disclosure (TL1 and TL2) against two prevalent commercial compositions (Product A and Product O).

FIG. 3 shows that the adhesive strength, measured in terms of contact time, of the representative compositions according to the present disclosure (TL1 and TL2) is greater than Product A and Product O. Specifically, the duration of adhesion under controlled conditions of TL1 and TL2 is about 6.3 hr and about 5.3 hr respectively, whereas the duration of adhesion of Product A and Product O is about 0.7 hr and about 0.04 hr respectively (Table 5). Briefly, a glass plate was coated with a micro-thin later of 10% gastric porcine mucin. Following the drying period (generally 30 min), a stainless steel weight of approximately 350 g was coated on one side with the formulation of interest. Next, approximately 500 g of pressure was applied for 30 seconds to the stainless steel weight to ensure intimate contact of the weight with the mucin-coated glass plate. Lastly, the plate, with the weight, was then inverted over a water bath maintained at body temperature (37° C.) and the time required for detachment was recorded for each formulations a minimum of three times. The detachment times were then averaged and reported as the mean detachment time±the standard deviation.

TABLE 5

Comparative Data Summary

| Product | AUC (sec · min) | Release rate (%/hr) | Adhesion Time (hr) |
|---|---|---|---|
| TL1 | 183 ± 41.68* | 2.43 ± 0.08 | 6.28 ± 0.99 |
| TL2 | 150 ± 18* | 2.97 ± 0.01 | 5.23 ± 0.90 |
| TL3 | NA | 1.41 ± 0.45 | NA |
| Product A | 47 ± 7.55 | 3.51 ± 0.44 | 0.65 ± 0.19 |
| Product O | 54 ± 18 | 1.40 ± 0.15 | 0.04 ± 0.01 |

*denotes a statistically significantly higher number (p < 0.05) when compared to product A or O.
*NA = not available Summary of the Comparative Study The above comparative study shows that when components are combined to form the composition according to the present disclosure, the combination of those components demonstrates a synergistic relationship, which provides the resulting composition with superior therapeutic effects for an extended period of time than existing commercial compositions.

The invention claimed is:

1. A method of delivering a topical anesthetic to a subject in need thereof, comprising administering at room temperature a liquid pharmaceutical composition comprising said topical anesthetic to a tissue of said subject, and maintaining said pharmaceutical composition in contact with said tissue of said subject for a time sufficient for the composition to reach body temperature and transition to a gel, wherein said pharmaceutical composition comprises
   a) from about 30 to about 70 weight parts of water;
   b) from about 10 to about 30 weight parts of polyethylene glycol (PEG) and/or from about 1 to about 10 weights parts of ethyl alcohol;
   c) from about 15 to about 25 weight parts of a copolymer having the following block structure:

HO—[CH2-CH2-O]a-[CH2-CH(CH3)-O]b-[CH2-CH2-O]a-H

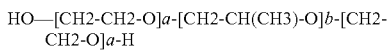

wherein the ratio of a:b is from about 1:1 to about 3:1, and the molecular weight of said copolymer is from about 9000 to about 16000; and
   d) from about 0.1 to about 3.0 weight parts of xanthan gum,
wherein, said composition turns from a liquid to a gel composition at a temperature between room temperature and the body temperature of said subject; has a capacity to adhere to said tissue when applied to said tissue; and has a capacity to bioerode and elute said active ingredient.

2. The method of delivering a pharmaceutical composition according to claim 1, wherein, said tissue is a surgical incision or a wound, further comprising closing said surgical incision or wound.

3. The method of delivering a pharmaceutical composition according to claim 1, wherein, said tissue is oral mucosa.

4. The method of claim 1, wherein weight parts of said water is from about 40 to about 60.

5. The method of claim 1, wherein weight parts of said polyethylene glycol is from about 15 to about 25, and/or weight parts of said ethyl alcohol is from about 4 to about 6.

6. The method of claim 1, wherein weight parts of said copolymer is from about 15 to about 20.

7. The method of claim 1, wherein weight parts of said xanthan gum is from about 0.1 to about 2.0.

8. The method of claim 1, wherein said topical anesthetic comprises benzocaine.

9. The method of claim 1, wherein said copolymer is a poloxamer.

10. The method of claim 1, wherein said copolymer is poloxamer 407.

11. The method of claim 1, wherein said polyethylene glycol is PEG 200.

12. The method of claim 1, wherein said composition comprises:
   a) from about 40 to about 45 weight parts of water;
   b) from about 15 to about 25 weight parts of polyethylene glycol, and/or from about 3 to about 6 weights parts of ethyl alcohol;
   c) from about 15 to about 20 weight parts of poloxamer 407;
   d) from about 1.5 to about 2.5 weight parts of xanthan gum; and
   e) about 20 weight parts of benzocaine.

13. The method of claim 1, wherein said composition comprises:
   a) about 41.5 weight parts of water;
   b) about 20 weight parts of polyethylene glycol, and/or about 4 weights parts of ethyl alcohol;
   c) about 16.5 weight parts of poloxamer 407;
   d) about 2.0 weight parts of xanthan gum; and
   e) about 20 weight parts of benzocaine.

14. The method of claim 1, wherein said composition comprises:
   a) about 43.5 weight parts of water;
   b) about 20 weight parts of polyethylene glycol, and/or about 4 weights parts of ethyl alcohol;
   c) about 15 weight parts of poloxamer 407;
   d) about 1.5 weight parts of xanthan gum; and
   e) about 20 weight parts of benzocaine.

15. The method of claim 1, wherein said active ingredient is released from said composition in zero order rate.

16. The method of claim 1, wherein said tissue comprises an open wound.

17. The method of claim 1, wherein the composition has a $T_{sol\text{-}gel}$ of from room temperature to 98.6 F.

18. The method of claim 1, wherein the composition increases in viscosity between room temperature and 98.6 F.

* * * * *